United States Patent [19]

Cassata

[11] 4,091,009

[45] May 23, 1978

[54] PROCESS FOR DEACTIVATING TOLUENE DIISOCYANATE DISTILLATION RESIDUE

[75] Inventor: John R. Cassata, Sulphur, La.

[73] Assignee: Olin Corporation, New Haven, Conn.

[21] Appl. No.: 780,562

[22] Filed: Mar. 23, 1977

Related U.S. Application Data

[63] Continuation-in-part of Ser. No. 714,533, Aug. 16, 1976, abandoned.

[51] Int. Cl.² ............... C07C 118/02; C07C 119/048
[52] U.S. Cl. ............................ 260/453 PH; 260/582
[58] Field of Search ...................... 260/453 PH, 582

[56] References Cited

U.S. PATENT DOCUMENTS

| | | | |
|---|---|---|---|
| 3,128,310 | 4/1964 | Koch | 260/582 |
| 3,210,395 | 10/1965 | McDougall | 260/453 PH |
| 3,225,094 | 12/1965 | Wolf | 260/582 |
| 3,331,876 | 7/1967 | Van Horn et al. | 260/582 |
| 3,499,035 | 3/1970 | Kober et al. | 260/453 PH |
| 3,636,030 | 1/1972 | Perkins | 260/453 SP |

*Primary Examiner*—Dolph H. Torrence
*Attorney, Agent, or Firm*—Robert J. Feltovic; Thomas P. O'Day; F. A. Iskander

[57] ABSTRACT

A selective process wherein toluene diisocyanate distillation residue is converted from a viscous liquid into an inert, granular solid by treatment with an aqueous solution of ammonia or an alkaline earth metal hydroxide.

16 Claims, No Drawings

PROCESS FOR DEACTIVATING TOLUENE DIISOCYANATE DISTILLATION RESIDUE

This application is a continuation-in-part of co-pending application Ser. No. 714,533, filed Aug. 16, 1976 and now abandoned.

This invention relates to the treatment and processing of the distillation residue which is obtained in the production of toluene diisocyanate. More particularly, the invention relates to a process for converting this residue into an inert, non-toxic and easy-to-handle granular solid.

Toluene diisocyanate is produced on a large commercial scale by a process which comprises reacting toluene diamine with excess phosgene usually in the presence of an organic solvent medium. An illustrative process is disclosed in U.S. Pat. No. 3,287,387. Along with toluene diisocyanate, the phosgenation product mixture usually comprises unreacted phosgene, solvent, hydrogen chloride by-product, and a relatively substantial proportion of side reaction products in the form of residual and high boiling materials.

Recovery of a substantial or major proportion of toluene diisocyanate from this mixture is achived by distillation which is usually carried in two or more steps to enable removal of the low-boiling components, e.g., the phosgene and solvent, first before recovering the toluene dissocyanate. The remaining residue from distillation is a viscous, fuming mixture which is difficult to transport or process. Thus on being pumped out for underground burial chemical processing or incineration, it gets thicker and thicker presumably as a result of further polymerization. As such, it eventually plugs up the lines making it difficult, if not impossible, to continue the pumping operation. Additionally, because of the toxic fumes emanating therefrom, this residue poses an environmental problem. Thus in processing it to underground burial, or incineration, or chemical treatment, special and costly steps must be taken to avoid polluting the atmosphere.

In order to recover toluene diamine values from the distillation residue, U.S. Pat. No. 3,128,310 discloses the concept of hydrolysis. According to the method described in this patent, the residue is heated with water to a temperature within the range of about 160°–250° C which effects it conversion to toluene diamine. Additionally, U.S. Pat. No. 3,331,876 discloses an improvement in this hydrolysis approach. Aimed at increasing the yield of toluene diamine, the improvement resides in effecting the hydrolysis at a temperature of 260°–350° C and in the presence of a relatively high proportion of alkali metal hydroxide.

It has also been disclosed in U.S. Pat. No. 3,210,395 to treat the toluene diisocyanate distillation residue containing the solvent and by-product tars with anhydrous ammonia. This treatment, which is effected at 100°–300° C or higher by bubbling anhydrous ammonia into the still residue, is said to result in precipitation of the bulk of the by-product tars which can then be easily removed by filtration.

Now a simple process has been found for deactivating the distillation residue which is obtained in the production of toluene diisocyanate. In accordance with the invention, this process comprises heating the residue to a temperature from about 60° to about 150° F in the presence of an aqueous solution of a base selected from the group consisting of ammonia, an alkaline earth metal hydroxide and a mixture thereof. By operating within these parameters, the residue is easily transformed from a viscous, fuming material into a non-toxic, inert, granular solid without resort to any grinding or other costly operations. As such, the granular product can then be easily disposed of or processed in open air without creating toxic hazards or polluting the atmosphere.

More in detail, the process of the invention can be carried out batch-wise or on a continuous basis. Generally continuous operation is preferred as it is more readily adapted to commercial practice in connection with the continuous production of toluene diisocyanate.

The process applies to the treatment of any residue which results from the distillation of the product of phosgenating toluene diamine. As commonly used in the commercial production of toluene diisocyanate, the toluene diamine is typically made up of a mixture of 2,4- and 2,6-isomers and may in addition contain traces of orthotoluene diamine. The distillation residue is usually a dark, viscous liquid which is substantially free of solvent. Along with varying traces of phosgene and by-product hydrochloric acid, it normally has a residual content of toluene diisocyanate ranging from about 15 to about 70% by weight, the balance being made up of high boiling and tarry by-products of the phosgenation reaction.

The basic material which is used in the process of the invention is ammonia or an alkaline earth metal hydroxide, e.g., calcium, magnesium or barium hydroxide. This is a critical feature of the invention, for it has been that the use of another base, namely, sodium hydroxide for example, results in transforming the residue into a product which, although solid, is a cohesive mass that is difficult to break up. Otherwise, it is generally within the broad contemplation of the invention to use other suitable organic bases as well, such as for example, cyclohexylamine, which is water-soluble. However, organic bases are relatively very costly and thus their use might diminish or outweigh the advantages which are realized by deactivating the residue.

A definitely preferred base for use in practicing the process of the invention is ammonia. In addition to its relatively low cost, it is particularly suitable for use in deactivating toluene diisocyanate distillation residues. For example, one of the additional advantages connected with its use is that it can subsequently be removed easily by simple distillation, and, if desired, it can be thereafter recycled for further use.

The basic material is used in aqueous solution form. To this end, it is preferable to first prepare the solution before it is brought into contact with the residue. However, if desired or if it is more convenient, the solution may be formed in-situ by separately adding the base and the water to the residue.

As indicated above, it is preferred to use an aqueous solution of ammonia in practicing the invention. Such a solution, whether prepared in advance or formed in-situ, can be provided for example, by mixing water with ammonia, or with a suitable ammonium salt such as ammonium carbonate, ammonium bicarbonate or the like. Thus it is to be understood that the term "aqueous solution of ammonia", as used in the specification and claims herein is clearly intended to mean and encompass an aqueous medium containing ammonia which medium is provided by any such techniques. In accordance with a particularly preferred embodiment of the invention, the aqueous solution of ammonia is provided from a mixture of water with ammonia or ammonium carbonate.

Generally, the concentration of the basic material in aqueous solution may be varied over a reasonably wide range, so long as it is effective in achieving the objectives of the invention. Illustratively, when an aqueous solution of ammonia is employed, this may have a concentration, on a dry basis, i.e., anhydrous ammonia, of about 2% by weight or more, such as from about 3 to about 20%, and preferably from about 5 to about 15% by weight; and the concentration of alkaline earth metal hydroxide in aqueous solution may range from about 3 to about 23%, and preferably from about 8 to about 14% by weight.

The proportion of the aqueous basic solution which is used per unit weight of the residue varies widely depending on the solution concentration and to a lesser degree on the make-up of the residue. Thus any suitable proportion may be used which is effective, when mixed with the residue and heated to within the temperatures specified herein, in transforming the residue from a viscous liquid to a granular solid. Illustratively, the solution is used in such a relative proportion as to provide, per every 100 parts by weight of residue, the equivalent of about 5–500, and preferably about 10–200, parts of base on a dry basis, i.e., anhydrous ammonia or dry alkaline earth metal hydroxide. In accordance with an especially preferred embodiment of the invention wherein aqueous ammonia is used, the proportion of solution is such as to provide the equivalent of about 15–50 parts of anhydrous ammonia per every 100 parts by weight of the residue.

A temperature within the relatively narrow range of about 60°–150° F is used in carrying out the process of the invention. This is another critical parameter; for it has been found that at temperatures below this range, the transformation of the viscous residue to a granular solid cannot be achieved satisfactorily; whereas, operating at temperatures above about 150° F will result in substantial agglomeration of the solids into large masses which would plug up the lines or generally create serious problems in subsequent processing.

To best achieve the objectives of the invention, it is definitely preferred to employ a temperature within a range that is above the lower limit of about 60° F and below the upper limit of about 150° F. This is because at temperatures corresponding to or approaching the lower limit, the residue deactivation may not be complete or may require a longer time to be completed. On the other hand, operating at temperatures corresponding to or approaching the upper limit specified above, may result in some solids agglomeration which, although manageable, would be undesirable or could present some difficulty in handling. Thus, while any temperatures within the above-specified range can be used to practice the invention, for the reasons given above and in order to achieve optimum results, it is preferred to employ a temperature from about 80° F to about 125° F and more preferably about 90°–112° F.

The process of the invention may be practiced using any type of reaction vessel which is equipped with an agitator, for adequately mixing the residue and the aqueous base, and with heat transfer means for maintaining the mixture at a temperature within the range specified above. Conveniently, a conventional stirred tank reactor may be utilized. Any convenient order of bringing together the residue and the aqueous base may be employed. For example, either material may be added to the other, or both materials may be simultaneously charged to the reactor. In a continuous operation which is linked to the continuous distillation of the toluene diamine phosgenation product, it is advantageous and preferred to add the residue, as obtained from the distillation still bottom, to the aqueous base.

Transformation of the residue from a dark, viscous liquid to a whitish, granular solid takes place fairly rapidly, i.e., usually within a few minutes, after it is mixed with the aqueous base. A slurry of this solid in the aqueous base results. This is then removed from the reactor. Thereafter, if desired, the solids may be separated by conventional methods, such as by centrifuging, preferably after the slurry has been cooled to about room temperature. The recovered, solids-free, liquid aqueous base may then be recycled for use in treating further residue. Ordinarily, the concentration of base in this liquid phase may become depleted to some extent. Accordingly, such concentration should be checked and adjusted if necessary before the solution is used again.

The deactivated, solid residue which is obtained by the process of the invention may be easily transported in slurry form for further processing or disposal. Alternatively, where the deactivated residue is separated as a solid from the slurry, it may be allowed to dry slowly in open air or, if quick drying is desired, it may be processed through a vacuum dryer at low temperature. The final product will be a granular, free-flowing solid which is inert and non-toxic. This can then be easily processed or disposed of in open-air without any danger of polluting the atmosphere or creating a toxic hazard. If desired, this granular material may subsequently be subjected to hydrolysis using prior art methods, in order to recover toluene diamine values therefrom.

The following examples are provided to illustrate the invention. The toluene diisocyanate distillation residue which is referred to and used throughout the examples was obtained by a conventional method, as described for example in U.S. Pat. No. 3,287,387 to Denton et al., for the commercial production of toluene diisocyanate. More specifically, this method involves (a) reacting, at about 125° C, excess phosgene with a solution of toluene diamine (mixture of 2,4- and 2,6-isomers) in monochlorobenzene solvent, (b) removing the monochlorobenzene, unreacted phosgene and by-product HCl from the phosgenation product, and (c) further distilling the remaining product to recover overhead pure toluene diisocyanate. The residue from this distillation is used in the examples.

Further in the examples, all parts and percentages are by weight unless otherwise specified.

EXAMPLE 1

Into a 3-neck, one-liter flask, equipped with a mechanical agitator, a heating mantle and a thermometer, there were placed 500 mls. of a 10% aqueous solution of ammonia, which solution had been prepared by bubbling anhydrous ammonia in water. Then about 80 grams of distillation residue were added gradually and thoroughly mixed in. Before addition, the temperature of the residue was 338° F. Upon being mixed with the room-temperature aqueous ammonia, a mixture temperature within the range of 95°–120° F was observed. This range was maintained, without external heating, by virtue of the exothermic nature of the reaction. Within 3–4 minutes of continuous stirring, the residue was transformed from a viscous, dark brown liquid to an off-white, particulate material suspended in the aqueous medium. The slurry was filtered and the resulting cake was allowed to dry in open air. A granular, inert product was thus obtained which was free-flowing and easy to handle or transport.

EXAMPLES 2-3

In these examples, the identical procedure of Example 1 was followed with one variation, namely, that of using aqueous calcium hydroxide in lieu of the aqueous ammonia. Specifically, in Example 2 a 22% aqueous solution of calcium hydroxide was used; and in Example 3, a 3% solution was used. In both examples, substantially the same result was obtained as noted in Example 1, although the granular product obtained in both Examples 2 and 3 after drying presumably contained varying but small amounts of calcium hydroxide.

Comparison 1

This comparison represents a further run as per Example 1 excpet that in lieu of the aqueous ammonia, a 10% aqueous solution of sodium hydroxide was used. As soon as the reactants were brought into intimate mixture, a rapid exotherm was observed with a practically instantaneous formation of a large, cohesive, and hard solid mass which could not be broken up by further agitation in the flash. This comparison demonstrates the practical drawback connected with using a basic material, other than one specified herein, in carrying out the process of the invention for deactivating the residue.

EXAMPLES 3-4

In these examples, the procedure of Example 1 was followed except for variations in temperature. Thus instead of using a temperature within the range of 95°-120° F in Example 3, room temperature was used; and in Example 4, a temperature of about 130° F was used. As a result, at the end of 4 minutes the product obtained in Example 3 consisted of larger granules. On close examination, these granules were found to be made up of a thin outer shell of deactivated residue surrounding a core of brown material representing substantially unreacted or still active, though solidified, residue. As for Example 4, an off-white, particulate, inactive solid product did form initially. However, in comparison to the product of Example 1, the product of Example 4 soon agglomerated into a larger mass which was more difficult to handle.

The results of Examples 3 and 4 demonstrate that by operating at temperatures approaching the outer limits set forth herein, while at least partial deactivation and solidification of the residue is achieved pursuant to the teachings of the invention, the practical results may be less than optimum. As such, operating at such temperatures may necessitate additional expedients, e.g., more violent mixing to bring about complete deactivation or to prevent substantial agglomeration. In another sense, the results of Examples 3 and 4 demonstrate the practical desirability of operating at a temperature with the preferred range of about 80°-125° F.

EXAMPLE 5

Again the identical procedure of Example 1 was followed. Here, however, the aqueous ammonia solution was prepared by dissolving ammonium carbonate (17.6% concentration) in water. Substantially the same result was obtained as noted in Example 1.

What is claimed is:

1. A process for converting into an inert, granular solid the substantially solvent-free residue which is obtained from the distillation of the product of phosgenating toluene diamine to the corresponding toluene diisocyanate, which process comprises heating said residue to a temperature from about 60° F to about 150° F in the presence of an aqueous solution of a base selected from the group consisting of ammonia and an alkaline earth metal hydroxide.

2. The process of claim 1 wherein said temperature is about 90°-112° F.

3. The process of claim 1 wherein an aqueous solution of ammonia is used.

4. The process of claim 3 wherein said solution is provided by mixing water with ammonia or ammonium carbonate.

5. The process of claim 1 wherein said aqueous solution is prepared in advance before being brought into contact with said residue.

6. The process of claim 1 wherein said temperature is about 80°-125° F.

7. The process of claim 6 wherein said alkaline earth metal hydroxide is calcium, magnesium or barium hydroxide.

8. The process of claim 6 wherein an aqueous solution of ammonia is used.

9. The process of claim 8 wherein the concentration of ammonia in said solution ranges from about 3 to about 20 percent by weight.

10. The process of claim 9 wherein said solution is employed in such a proportion as to provide the equivalent of about 10-200 parts of anhydrous ammonia per every 100 parts by weight of said residue.

11. The process of claim 10 wherein said temperature range is about 90°-120° F.

12. The process of claim 11 wherein said aqueous solution of ammonia is provided by mixing water with ammonia or ammonium carbonate.

13. The process of claim 12 wherein said aqueous solution of ammonia is prepared in advance before being brought into contact with said residue.

14. The process of claim 13 wherein the concentration of ammonia in said aqueous solution ranges from about 5 to about 15 percent by weight.

15. The process of claim 14 wherein said solution is employed in such a proportion as to provide the equivalent of about 15-50 parts of anhydrous ammonia per every 100 parts by weight of said residue.

16. The process of claim 1 which includes the added step of separating said solid from said aqueous solution.

* * * * *